US007615370B2

(12) United States Patent
Streit et al.

(10) Patent No.: US 7,615,370 B2
(45) Date of Patent: Nov. 10, 2009

(54) SYSTEM HAVING DEVICE FOR PREVENTING AIR BUBBLES IN A HYBRIDIZATION CHAMBER AND CORRESPONDING METHOD

(75) Inventors: Wolfgang Streit, Hallein (AT); Gyoergy Wenczel, Seekirchen (AT); Waltraud Lamprecht, Salzburg (AT); Heribert Eglauer, Berchtesgaden (DE)

(73) Assignee: Tecan Trading AG, Mannedorf (CH)

( * ) Notice: Subject to any disclaimer, the term of this patent is extended or adjusted under 35 U.S.C. 154(b) by 876 days.

(21) Appl. No.: 10/931,432

(22) Filed: Sep. 1, 2004

(65) Prior Publication Data

US 2006/0008812 A1 Jan. 12, 2006

(30) Foreign Application Priority Data

Jul. 8, 2004 (CH) .................................... 1144/04
Aug. 4, 2004 (DE) .................. 20 2004 012 163 U

(51) Int. Cl.
*C12M 1/34* (2006.01)
*C12M 3/00* (2006.01)

(52) U.S. Cl. ............. 435/287.2; 435/287.1; 435/286.7; 435/288.5

(58) Field of Classification Search .... 435/287.1–288.5
See application file for complete search history.

(56) References Cited

U.S. PATENT DOCUMENTS

| | | | | |
|---|---|---|---|---|
| 5,922,591 | A | 7/1999 | Anderson et al. | |
| 6,186,659 | B1 | 2/2001 | Schembri | |
| 6,238,910 | B1 | 5/2001 | Custance et al. | |
| 6,458,526 | B1 | 10/2002 | Schembri et al. | |
| 6,753,169 | B2 | 6/2004 | Hess et al. | |
| 2002/0009015 | A1 | 1/2002 | Laugharn et al. | |
| 2002/0075363 | A1 | 6/2002 | McNeely et al. | |
| 2003/0013184 | A1* | 1/2003 | Streit et al. | 435/287.2 |

FOREIGN PATENT DOCUMENTS

| | | |
|---|---|---|
| EP | 1 260 265 | 11/2002 |
| WO | WO 2004/052527 | 6/2004 |

* cited by examiner

*Primary Examiner*—Walter D Griffin
*Assistant Examiner*—Shanta G Doe
(74) *Attorney, Agent, or Firm*—Notaro & Michalos P.C.

(57) ABSTRACT

The present invention relates to a system (1) having hybridization chambers (5) for hybridizing nucleic acid samples, proteins, or tissue sections immobilized on slides (27), each hybridization chamber (5) being defined as an essentially gap-shaped chamber, which is essentially fillable with a liquid, between one of these slides (27) and a cover (26), and the cover (26) being positioned in relation to the slide (27) in such a way that the hybridization chamber (5) is sealed to the surrounding air, the system (1) including a device for preventing air bubbles in the hybridization chambers (5). The system according to the present invention is distinguished in that this device for preventing air bubbles in the hybridization chambers (5) is implemented as a pressure device to build up a chamber pressure in the hybridization chambers (5), this chamber pressure lying above the normal atmospheric pressure existing in the surrounding air. The present invention additionally relates to a method for preventing air bubbles in the hybridization chambers (5) of such a system (1) and is distinguished in that, using a pressure device of this system (1), a chamber pressure is implemented in the hybridization chambers (5) which lies above the normal atmospheric pressure existing in the surrounding air.

7 Claims, 2 Drawing Sheets

SYSTEM HAVING DEVICE FOR PREVENTING AIR BUBBLES IN A HYBRIDIZATION CHAMBER AND CORRESPONDING METHOD

CROSS-REFERENCE TO RELATED APPLICATIONS

This patent application claims priority of the German Utility Patent Application No. DE 20 2004 012 163.8 filed on Aug. 4, 2004 and of the Swiss Patent Application No. CH 2004 1144/04 filed on Jul. 8, 2004.

FIELD AND BACKGROUND OF THE INVENTION

The present invention relates to a system having hybridization chambers for hybridizing nucleic acid samples, proteins, or tissue sections immobilized on slides. In this case, each hybridization chamber is defined between one of these slides and a cover as an essentially gap-shaped chamber which is essentially fillable with a liquid. Each cover is positioned in relation to a slide in such a way that the hybridization chamber is sealed to the surrounding air. Such a system includes a device for preventing air bubbles in the hybridization chambers. In addition, the present invention relates to a corresponding method for preventing air bubbles in the hybridization chamber of a system for hybridizing nucleic acid samples, proteins, or tissue sections immobilized on slides. According to this method, all essentially gap-shaped hybridization chambers positioned between this slide and a cover are essentially filled with a liquid. In this case, the cover is positioned in relation to the slide so that the hybridization chamber is sealed to the surrounding air.

The use of DNA samples (DNA=deoxyribonucleic acid) and particularly microarrays of such samples provides an important technology to research for simultaneous analysis of thousands of genes. This technology includes the immobilization of DNA samples from many genes on a solid substrate surface, on a glass slide for a light microscope, for example. The DNA samples are preferably positioned in an array of sample spots or "spots", i.e., in a two-dimensional grid on the substrate and, on the basis of a specific position within such an array, the origin of the corresponding DNA sample may be concluded later. The technology typically includes contacting the DNA sample array with RNA specimen suspensions and/or solutions (RNA=ribonucleic acid) in order to thus detect specific nucleotide sequences in the DNA samples. Typically, specimen suspensions which contain DNA, cDNA, and/or proteins or polypeptides are also used.

RNA specimens may be provided with a so-called "tag" or "label", i.e., a molecule which emits a fluorescent light having a specific wavelength, for example. Immobilized samples may also include samples containing amino acids (e.g., proteins, peptides) or nucleic acids (e.g., cDNA, RNA). Any arbitrary molecules and/or chemical compounds which hybridize with the immobilized samples or otherwise bond thereto may be included in the specimen added to the immobilized samples.

Under good experimental conditions, the RNA specimens hybridize and/or bond to the immobilized DNA samples and form hybrid DNA-RNA strands together therewith. For each of the immobilized DNA samples and for special RNA specimens, differences in the hybridization among the DNA samples may be determined by measuring the intensity and wavelength dependence of the fluorescence of each individual microarray element and it may thus be found out whether the degree of gene expression varies in the DNA samples assayed. Using DNA microarrays, extensive statements may be made about the expression of large quantities of genes and their expression pattern, although only slight quantities of biological material must be used.

DNA microarrays have been established as successful tools and the devices for performing DNA hybridization are being improved continuously (cf., for example, U.S. Pat. No. 6,238,910 or EP 1 260 265 A1 from the applicant of the present application). These documents disclose a device for providing a hybridization chamber for hybridizing nucleic acid samples on the slide. These devices are implemented as movable in relation to the slide and include an annular seal or sealing surface for sealing the gap-shaped hybridization chamber in relation to the surrounding air, the seal or sealing surface being applied to a surface of this slide. In addition, these devices include lines for supplying and removing media into and from, respectively, the hybridization chamber, as well as a sample supply. An improved temperature control and movement of the liquid having, for example, RNA specimens in relation to the DNA samples immobilized on the slide are also disclosed.

It happens again and again that air bubbles arise when liquids are introduced into the hybridization chamber or even later. However, the attempt has been made (cf., for example, U.S. Pat. No. 6,186,659) to use air bubbles intentionally as an agitation means in order to achieve more thorough mixing of the reagents in the hybridization chamber. In general, however, air bubbles present in the hybridization medium are not desired because they interfere with the liquid film over the immobilized samples, which is usually very thin. This may lead to inhomogeneity of the distribution of reagents in the hybridization medium and therefore to corruption of the hybridization results; in the worst case, larger air bubbles even displace the hybridization medium from parts of the samples immobilized on the slide.

In addition, numerous methods are known from the related art for preventing the spontaneous occurrence of air bubbles or the existence thereof in the chamber. Thus, for example, a non-parallel arrangement of the slide and cover defining the hybridization chamber is suggested (cf. U.S. Pat. No. 5,922,591), or the hybridization media are transported out of the chamber and back in during the entire hybridization process. Admixing agents which reduce the surface tension to the hybridization medium or treating the surfaces of the chamber with water-repellent chemical compounds, with the goal of preventing the formation of air bubbles, is also known.

An arrangement is known from U.S. Pat. No. 6,458,526, using which "bubble halves 140", made of a gas saturated with solvent, which project into the hybridization chamber, are produced. These "bubble halves" are actually boundary surfaces, shaped like spherical caps, of gas chambers having a defined radius of curvature. These "bubble halves" are located at defined points of the chamber where they may not interfere with the hybridization of the samples. A solvent 160, which is contained in the hybridization medium, is located in a compartment separated from the hybridization chamber. Via this solvent, a saturated atmosphere 150 is maintained, which is constantly connected to the gas chambers behind the "bubble halves 140" (cf. FIG. 2 in U.S. Pat. No. 6,458,526). Therefore, an atmosphere saturated with the solvent is constantly brought to the boundary surfaces shaped like spherical caps and the partial pressure of the solvent present in the hybridization medium is thus influenced so that any air bubbles present shrink and are eliminated. This method has the disadvantage that these boundary surfaces shaped like spherical caps must be provided and maintained using special devices.

SUMMARY OF THE INVENTION

The object of the present invention relates to providing an alternative system and/or an alternative method, using which the formation of air bubbles in a hybridization chamber may be prevented in a simple way.

This object is achieved according to a first aspect of the claimed invention in that a system as described at the beginning includes a pressure device for building up a pressure in the hybridization chamber, which lies above the normal atmospheric pressure existing in the surrounding air. This object is achieved according to a second aspect of the invention in that, using a pressure device in a system as described in the beginning, a pressure is built up in the hybridization chamber which lies above the normal atmospheric pressure existing in the surrounding air. Additional preferred features according to the present invention result from the dependent claims.

The system according to the present invention and the method according to the present invention will now be explained in detail on the basis of a schematic drawing of exemplary embodiments, which is not to restrict the scope of the present invention.

DESCRIPTION OF PREFERRED EMBODIMENTS

Figure 1:
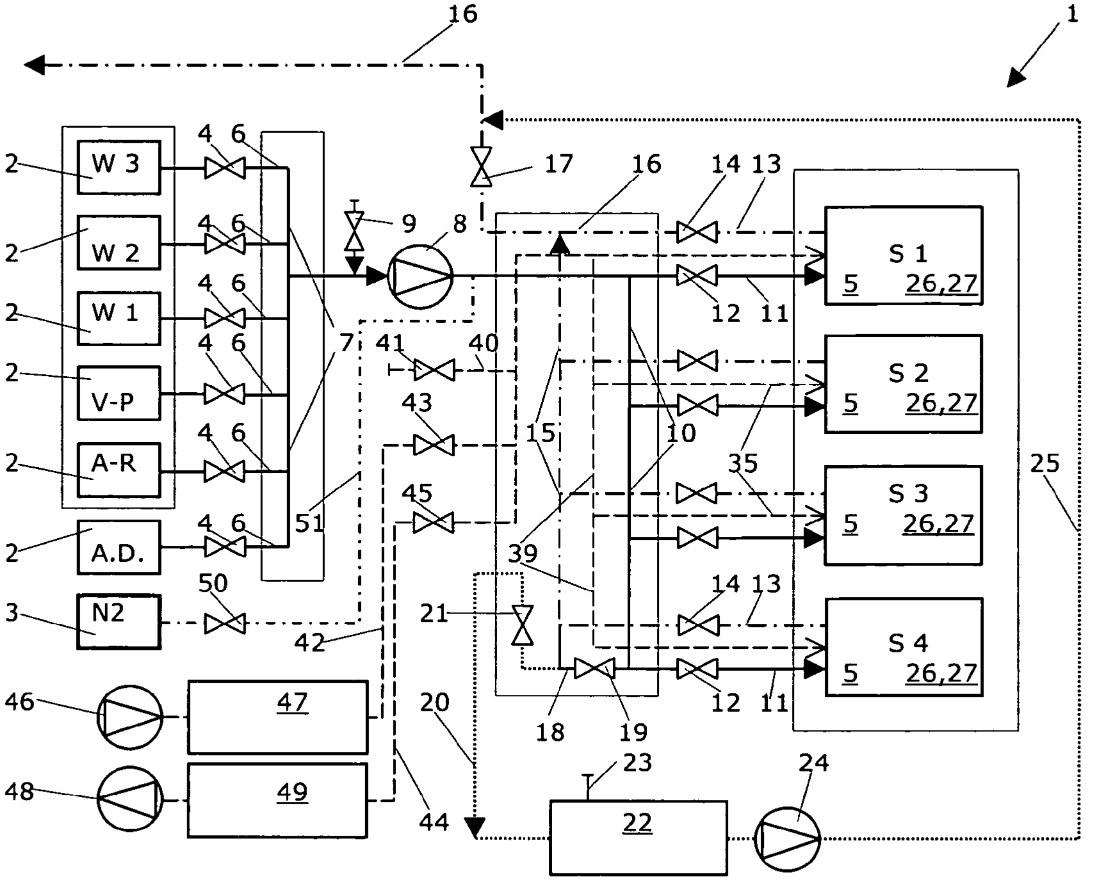
FIG. 1 shows a schematic diagram of a device and/or system capable of executing the method according to the present invention.

FIG. 1 shows a schematic diagram of a system 1 capable of executing the method according to the present invention. A number of vessels 2 for storing liquid hybridization media, such as washing liquids (W 3, W 2, W 1), pre-hybridization buffer (V-P), alcohol cleaning liquid (A-R), distilled water (A.D.), and a container 3 having inert gas (N2) are shown on the left side of this schematic diagram. An individual valve 4 is connected downstream from each of these vessels 2, via which these media may be supplied to the hybridization chambers 5 (S 1, S 2, S 3, S 4) (shown on the right side). The media lines 6 including the valve 4 discharge into a collection line 7, which in turn discharges into a feed pump 8, which a ventilation valve 9 is connected upstream from. This feed pump 8 sucks liquid media out of the vessels 2 via the collection line 7 and pumps it via the distribution line 10 into the inlet lines 11, which discharge into the hybridization chambers 5 via an inlet valve 12. The hybridization media leave the hybridization chambers 5 via an outlet line 13, each of which includes an outlet valve 14 and discharges into a collection line 15. This collection line 15 discharges in turn into a waste line 16, which is closable using a waste valve 17. The distribution line 10 and the collection line 15 may communicate with one another via a connection line 18 and a connection valve 19. A relief line 20 having a relief valve 21 branches off from this connection line 18 and discharges into a collection container 22 having an aeration and/or ventilation opening 23. A feed pump 24, which is connected via a transition line 25 to the waste line 16, is connected downstream from the collection container 22.

For better distribution of the hybridization media in the hybridization chambers 5, the system 1 is equipped with an agitation mechanism and/or with an agitation device 32, as is known from European Patent Application EP 1 260 265 A1 of the applicant of the present patent application. Reference is expressly made here to the content of this patent application EP 1 260 265 A1, so that this content is considered part of the present patent application.

Figure 2:
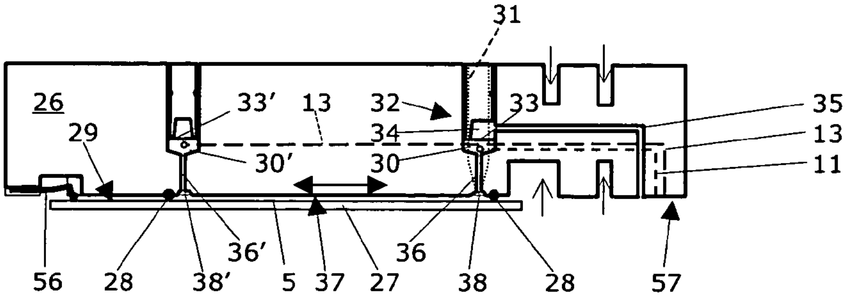
FIG. 2 shows a vertical longitudinal section through a system having a hybridization chamber corresponding to FIG. 1 from EP 1 260 265 A1.

FIG. 2 shows a vertical longitudinal section through a hybridization chamber 5, corresponding to FIG. 1 from EP 1 260 265 A1. The cover 26 of this arrangement is movable in relation to the slide 27 (implemented here as pivotable around an axis), so that the hybridization chamber 5 may be opened and closed through a simple movement. An annular sealing surface 28 is used for sealing the hybridization chamber 5 by being applied to a surface 29 of this slide 27. This sealing surface 28 may be a recessed surface of the cover 26 which lies flat on the surface 29 of the slide 27; alternatively, a lip seal may also be used, for example. However, an O-ring seal is preferably used as the sealing surface 28. The arrangement includes lines 11, 13 for supplying and removing media to and from, respectively, the hybridization chamber 5. Such media may be reagents for performing the hybridization reaction, such as washing liquids or buffer solutions, or even inert gases (such as nitrogen) for drying the hybridization products on the slide 27 and/or for purging the hybridization chamber 5 and the media lines 11, 13. These supply and/or removal lines 11, 13 for hybridization media preferably each discharge into an agitation chamber 30, 30'. The arrangement additionally includes a closable specimen supply 31, through which liquids containing RNA or other specimen liquids may be pipetted in manually. The specimen supply 31 is preferably closed using a plastic plug (not shown). Alternatively, an automatic and/or robotic specimen supply may be provided, as is disclosed in different embodiments in EP 1 260 265 A1.

The arrangement includes a medium-separating agitation device 32 for moving liquids in relation to samples of nucleic acids, proteins, or tissue sections immobilized on the surface 29 of the slides 27. In the embodiment shown in FIG. 2, the agitation device 32 of the arrangement includes a membrane 33. This membrane 33 separates a pressure chamber 34, which is implemented so it is fillable with a pressure fluid (gas or liquid) via a pressure line 35, from an agitation chamber 30, which is connected to the hybridization chamber 5 via an agitation line 36. After reaching the thermal equilibrium of the arrangement, adding a specific volume of RNA specimen liquid, and closing the specimen supply 31, air or another gas (but it may also be a liquid) is preferably introduced into the pressure chamber 34 via pressure line 35 or drained therefrom in pulses, so that the membrane 33 deflects in the same rhythm and accordingly shrinks and/or enlarges the agitation chamber 30. The specimen liquid is thus moved against one or the other end in the hybridization chamber 5 in the same rhythm of the overpressure or partial vacuum and relaxing, where a transverse flow channel 38, 38' is preferably located on the surface 37 of the cover 26 facing toward the inside of the hybridization chamber 5.

These transverse flow channels 38, 38' make the transverse distribution of the RNA molecules contained in the specimen solution easier. This causes the specimen liquid and/or the wash liquids to be distributed homogeneously over the entire volume present in the hybridization chamber 5. In addition, the transverse flow channels 38, 38' are also used as the liquid reservoir, so that parts of the hybridization chamber 5 are not unintentionally left dry during the reciprocating motion (solid double arrow) generated in the agitation device 32 incorporated in the device.

Preferably, a second agitation chamber 30', also provided with a membrane 33', is connected via a second agitation line 36' to the hybridization chamber 5. If a pressure pulse output onto the pressure chamber 34 presses the first membrane 33 into the first agitation chamber 30, this pulse is transmitted to the specimen liquid in the hybridization chamber 5 via the first agitation line 36. The specimen liquid yields somewhat toward the second agitation line 36' (and may even partially fill it) and increases the pressure in the second agitation chamber 30'. The second membrane 33' thus deflects upward and is elastically stretched at the same time. As soon as the excess pressure in the pressure chamber 34 is relieved, both membranes 33, 33' spring back into their rest position and move the specimen liquid in the hybridization chamber 4 in the opposite direction. Through this reciprocating motion, a specimen liquid having a minimal volume (in the range of approximately 100 μl) may be distributed practically homogeneously in the hybridization chamber 4 in less than one minute using the arrangement shown. Preferably, a partial vacuum is generated in the pressure chamber 34 immediately following the pressure reduction in the pressure chamber 34, so that the backward motion of the specimen liquid into the hybridization chamber 5 opposing the preceding pressure pulse is further amplified.

Figure 3:
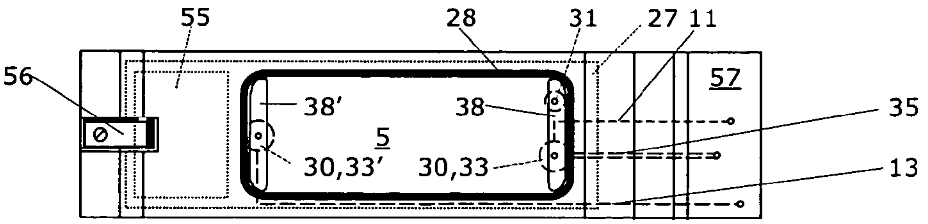
FIG. 3 shows a schematic view of a system having a hybridization chamber, seen from below, corresponding to FIG. 2.

FIG. 3 shows a horizontal projection of the arrangement of FIG. 2, seen from below. The O-ring seal 28 laterally delimits the hybridization chamber 5, which has a transverse flow channel 38, 38', which are provided as depressions in the surface 37 of the cover 26, on each of its diametrically opposing ends. The slide 27 (a glass slide for light microscopy here) and its grip area 55 are shown dashed. The hold-down spring 56, which presses on the grip area 55 of the slide 27, is also clearly visible. When the hybridization chamber 5 is opened, this hold-down spring 56 makes automatically separating the slide 27 from the cover 26 easier. The layout of the inlet line 11, the outlet line 13, and the pressure line 35 and the arrangement of the agitation chamber 30, 30' and the specimen supply 31 are also obvious. The agitation lines 36, 36' and the specimen supply 31 discharge into the transverse flow channels 38, 38'.

All lines 11, 13, 35 for supplying and/or removing media preferably discharge into a shared connection plane 57 of the cover 26, which is positioned essentially parallel to the hybridization chamber 5 and preferably at the same height as the hybridization chamber 5. The discharge openings of the lines 11, 13, 35 may be positioned offset to one another (as shown) or on a line (not shown) running transversely to the device 1. Recesses (blank arrows, cf. FIG. 2) reduce the heat flow from or to the cover 26.

The pressure lines 35, one of which is intended for each of the hybridization chambers 5, are shown dashed in FIG. 1 and originate from a pressure distribution line 39. An equalization line 40 having an equalization valve 41, an excess pressure supply line 42 having an excess pressure valve 43 and a partial vacuum supply line 44 having a partial vacuum valve 45 discharge into this pressure distribution line 39. The excess pressure is preferably generated using a cost-effective gas (air, for example) in an excess pressure pump 46, stored in an excess pressure container 47, and fed into the excess pressure supply line 42. The partial vacuum is generated in a partial vacuum pump 48, stored in a partial vacuum container 49, and fed into the partial vacuum supply line 44.

The inert gas container 3 is connected via a gas valve 50 and a gas line 51 to the distribution line 10, which discharges into the hybridization chambers 5 via inlet lines 11 and one inlet valve 12 each. All hybridization chambers 5 (individually or groups, depending on the valve settings) may be purged using inert gas (e.g., nitrogen gas) via the distribution line 10, and the inlet lines 11 via the outlet line 13 and the collection line 15.

If only the gas valve 50, the connection valve 19, and the relief valve 21 are opened, the distribution line 10 may be purged into the collection container 22. If only the gas valve 50, the connection valve 19, and the waste valve 17 are opened, the distribution line 10 and the collection line 15 may be purged via the waste line 16.

Figure 4:
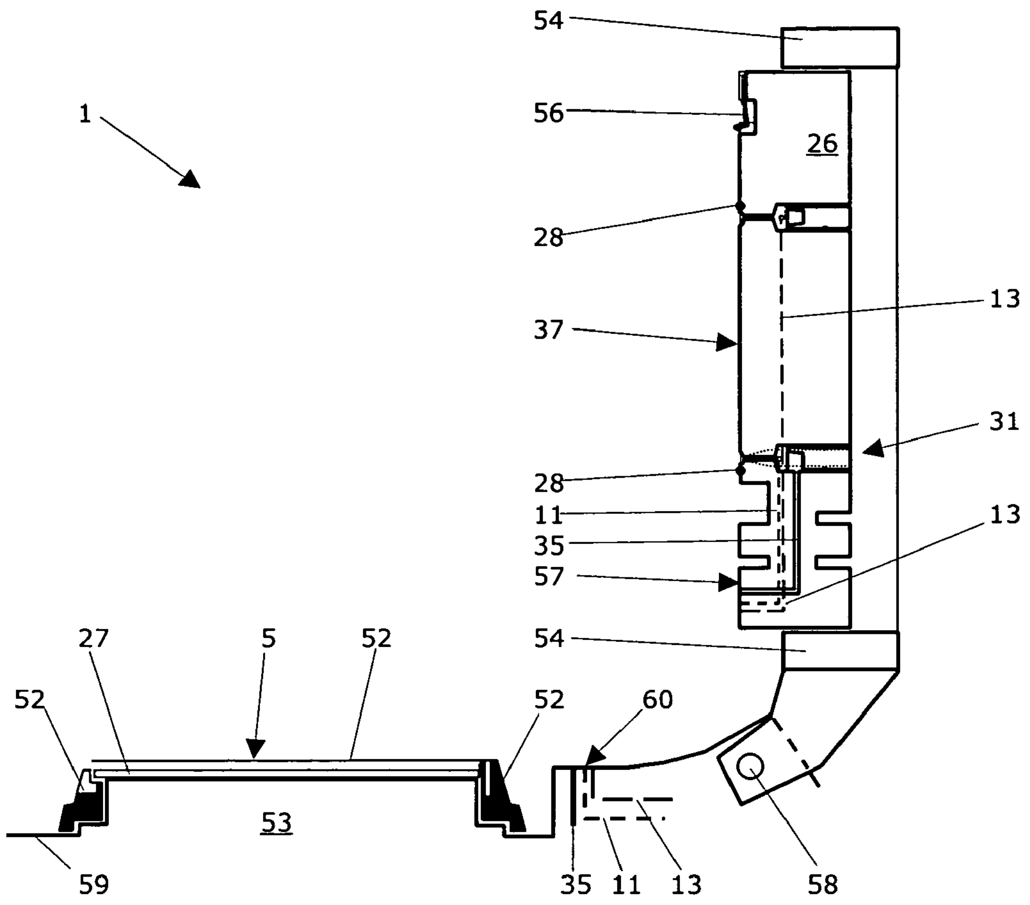
FIG. 4 shows a vertical longitudinal section, corresponding to FIG. 2, through a system having a hybridization chamber, with the cover of the system folded up.

FIG. 4 shows a vertical longitudinal section, corresponding to FIG. 2, through an arrangement having a hybridization chamber 5, the folding frame 54, having the cover 26 of the system 1 inserted therein, being folded up. The covers 26 are preferably positioned parallel to one another and in a group of four, because this arrangement permits dimensions for a contact plate 53 of the temperature control thermostat on which a transport frame 52 of the size of a microplate having four slides 27 positioned parallel to one another fits precisely. Each of these groups of four is assigned to a contact plate 53 connected to a temperature control unit. Such a contact plate 53 is thus implemented to accommodate the four slides 27 of a transport frame 52 flat. The frame 52 includes lengthwise walls, transverse walls, and intermediate walls running essentially parallel to the transverse walls. These walls enclose openings which completely penetrate the frame 52, these openings allowing direct contact between the contact plate 53 of the thermostat and the slides 27. Because the slides 27 are held softly and elastically in the frame 52 and because the contact plate 53 is implemented so that the frame 52 may be lowered somewhat in relation thereto, the slides 27 lie directly on the surface of the contact plate 53. Each group of four of a method unit includes a folding frame 54, pivotable around an axis 58 and lockable in relation to a baseplate 59, having four seats, a cover 26 being insertable in each of these seats. Each such method unit additionally includes a connection plate 60 for the sealed connection of an inlet line 11, outlet line 13, and pressure line 35 of the system 1 with the inlet line 11, outlet line 13, and pressure line 35 of a cover 26. O-rings positioned on the system side are preferred as seals for these connections (not shown).

Figure 5:
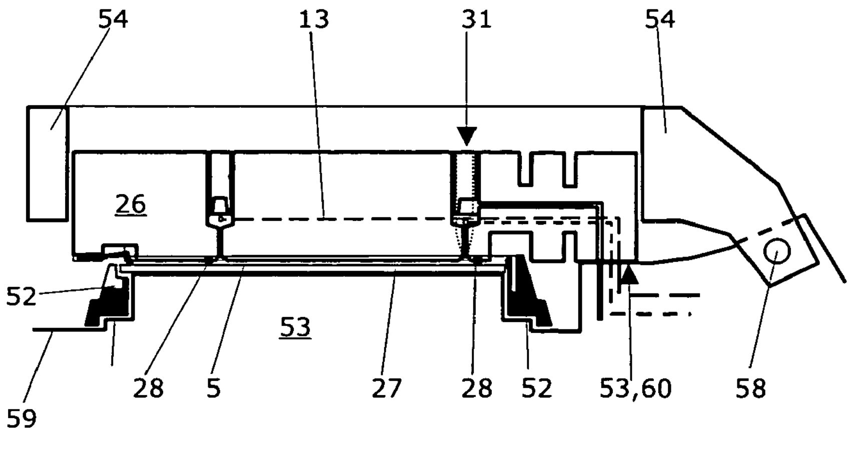
FIG. 5 shows a vertical longitudinal section, corresponding to FIG. 2, through a system having a hybridization chamber, with the cover of the system closed.

FIG. 5 shows a vertical longitudinal section, corresponding to FIG. 2, through an arrangement having a hybridization chamber 5, the cover 26 of the system, inserted into a folding frame 54, being closed. All four hybridization chambers 5 of a group of four defined by a contact plate 53 and such a folding frame 54 are thus assigned to the temperature control of a temperature control unit. Each group of four of a method unit includes, as described above, a folding frame 54, pivotable around an axis 58 and lockable in relation to a baseplate 59, having four seats, a cover 26 being insertable into each of these seats. In order to ensure that the cover 26 may be placed plane-parallel to the slides 27, the folding frame 54 additionally has a middle joint (not shown) having mobility parallel to the axis 58. An additional pressure, which may be produced via screws, rocker arms, or similar known devices (not shown), is exerted on the cover 26 via the folding frame 54 so that the seals 28 reliably seal the hybridization chambers 5.

The present invention is based on the recognition that the spontaneous occurrence of air bubbles during hybridization may be prevented by generating excess pressure in the hybridization chamber 5. In this case, the chamber pressure is to be above the normal atmospheric pressure existing in the surrounding air. A chamber pressure which is at least 100 mbar up to at most 1.4 bar higher than the surrounding pressure is preferred. Even higher pressures are possible in the chamber if a contact pressure which is sufficiently greater to keep the chamber sealed counteracts them.

Air bubbles actually no longer arise during hybridization under these pressure conditions. The functional mechanism which this phenomenon is based on has not been completely explained. However, it is assumed that the increased pressure determines and/or defines the diffusion direction in the region of the O-ring seal 28, so that gas molecules of the surrounding air may no longer diffuse into the hybridization chamber 5. In addition, there is certainly a shift of the phase boundaries in the hybridization medium because of their pressure dependence, so that spontaneous air bubble formation is suppressed. In connection with the present invention, all gas bubbles in the hybridization medium—notwithstanding the generation process in the hybridization chamber 5—are therefore referred to as “air bubbles”.

According to the present invention, the required excess pressure in the hybridization chambers 5 may be achieved using a liquid, for example, using a hybridization medium from one of the vessels 2 pressed into the hybridization chambers 5 using the feed pump 8 (cf. FIG. 1). If a system 1 including this hybridization chamber 5 has an agitation device 32 for moving the hybridization media in relation to the immobilized samples, this system preferably also includes a spring element which elastically counteracts the pressure differences generated by the agitation device 32. Such a spring element may be an elastic tubular part (not shown) in a corresponding supply or removal line to the hybridization chamber 5; however, an elastically impinged expansion vessel (not shown) may also be provided, which is connected via a line to the hybridization chamber 5.

As an alternative to this, inert gas may also be pressed out of the container 3 into the distribution line 10 and the inlet lines 11 and the required pressure may be built up in the hybridization chambers 5, which are already filled with samples and hybridization media, via one inlet valve 12 each. Inert gases such as $N_2$ (nitrogen), which do not have any chemical interaction or reactions with the hybridization media, are preferred. In addition, it may be advantageous if the inert gases are not soluble in the hybridization media. There is also the possibility of introducing gas originating from a pressure pump and a pressure container (similar to the elements identified with 46 and 47 in FIG. 1) into the distribution line 10. After the pressure buildup, all valves may be closed again and the hybridization may be performed. In this case, the gas cushion built up in this way, which is directly connected to the liquid volumes used for the hybridization, is used as a spring element for elastically counteracting the agitation pressure differences. If necessary, because of a minimal but constant pressure loss via the O-ring seals 28, for example, the required chamber pressure may be corrected sporadically or renewed and/or kept constant during the hybridization, which typically takes many hours. For this purpose, one or both of the valves 12, 14 (cf. FIG. 1) may alternately also be kept open.

A further alternative (not shown in the figures) is to connect a pressure pump and a pressure container (similar to the elements identified with 46 and 47 in FIG. 1) or a gas container (such as the $N_2$ container 3 in FIG. 1) to the collection line 15 and to build up the pressure in the hybridization chambers 5 by opening the outlet valves 14. An additional alternative for providing a gas cushion which is used as a spring element to elastically counteract the agitation pressure differences is to conduct gas originating from a pressure pump and a pressure container (similar to the elements identified with 46 and 47 in FIG. 1) or a gas container (such as the $N_2$ container 3 in FIG. 1) into one of the lines which discharges into at least one of the distribution line 10 or collection line 15. Correspondingly, one or both of the valves 12, 14 (cf. FIG. 1) may be kept open.

If a system 1 having arrangements which (as described above) include two agitation membranes 33, 33' is used, the agitation device 32 may be used during the preparatory agitation of the hybridization media in the hybridization chambers 5 or even during the hybridization itself. For this purpose, an agitation pressure must simply be generated in the pressure chamber 34 which is approximately 0.5 to 1 bar higher than the desired chamber pressure of 100 mbar to 1.4 bar above the surrounding pressure. The pressure to be applied for the agitation thus moves (depending on the surrounding pressure) in the range from approximately 0.6-2.4 bar. In this case, the second membrane 33' forms a spring element which elastically counteracts this agitation pressure.

Typically, hybridization is performed as follows:

a) Purging air bubbles and liquid residues out of the distribution line 10 and the collection line 15. For this purpose, only the valves 4 (A.D.), 19, and 17 are opened and distilled water is pumped out of the vessel 2 (A.D.) via the valve 4 (A.D.) into the distribution line 10 using the feed pump 8. The distilled water flows through the connection valve 19 into the collection line 15 and from there via the waste valve 17 into the waste line 16.

The hybridization chambers 5 are constructed simultaneously. This is performed by laying slides 27 (preferably held in a transport frame 52) having samples immobilized thereon on the contact plate 53 of a thermostat, inserting covers 26 into the folding frame 54 of the system 1 for hybridizing nucleic acid samples, proteins, or tissue sections immobilized on slides 27, and closing the hybridization chambers 5 by folding down the cover 26 onto the slides 24 (cf. FIGS. 4 and 5). This folding down connects the ends of the inlet lines 11, the outlet lines 12, and the pressure lines 35 of the agitation device 32 of each individual hybridization chamber 5 to the corresponding line ends of the system 1. Preferably, four covers 26 are inserted into one folding frame—corresponding to the four slides 27 received in a transport frame 52.

b) Filling and temperature control of the hybridization chambers 5 using pre-hybridization buffer. For this purpose, only the valves 4 (V-P), 12, 14, and 17 are opened and pre-hybridization buffer is pumped, using the feed pump 8, out of the vessel 2 (V-P) via the valve 4 (V-P) into the distribution line 10 and from there via the inlet valves 12 into the hybridization chambers 5. A part of the pre-hybridization buffer leaves the hybridization chambers 5 via the outlet valves 14 and the collection line 15 and reaches the waste line 16 via the waste valve 17. This procedure requires special care, because air bubbles may be carried along into the hybridization chambers 5 for the first time here.

c) Purging the distribution line 10 and the collection line 15. For this purpose, only the valves 9, 19, and 17 are opened and air is suctioned in via the aeration valves 9 using the feed pump 8 and pumped via the distribution line 10 and the connection valve 19 into the collection line 15 and from there via the waste valve 17 into the waste line 16.

d) Feeding samples into the hybridization chambers 5. For this purpose, only the valves 14 and 21 are opened. The samples are pressed using a pipette into the hybridization chambers 5 via the specimen supply 31 in the cover 26. A corresponding volume of pre-hybridization buffer is thus displaced out of the hybridization chambers 5 into the outlet line 13 having the open outlet valves 14. This in turn displaces a corresponding volume of air out of the collection line 15. This displaced air flows through the open relief valve 21 into the relief line 20 and reaches the collection container 22, which it leaves via the ventilation opening 23. This procedure requires special care, because air bubbles may be carried along into the hybridization chambers 5 for the second time here.

e) Uniform distribution of the hybridization media in the hybridization chambers 5 and in relation to the samples immobilized on the slides 27. For this purpose, all valves are first closed. The chamber pressure is then elevated as already described and the agitation device 32 is put into operation.

All air bubbles possibly present in the hybridization chambers 5 are eliminated during this pressure increase.

f) Hybridization of the samples for 17 hours, for example. During the hybridization, the media in the hybridization chambers 5 may be agitated constantly or intermittently. This procedure requires special care because air bubbles may arise spontaneously in the hybridization chambers 5 here. In order to prevent this, the chamber pressure may be adapted for corrective purposes and kept constant and/or changed according to an individual program during the hybridization. Such a program may define the elevation and reduction of the chamber pressure in specific pressure and time steps, so that careful hybridization of the samples which require such special treatment is ensured.

g) Washing the hybridized samples using buffers. For this purpose, first the chamber pressure is regulated to normal pressure by opening the outlet valves 14 and the waste valve 17. Washing liquids are then pumped sequentially and as needed using the feed pump 8 out of the vessels 2 through the appropriately opened valves 4 in the distribution line 10 and from there via the opened inlet valves 12 and the inlet lines 11 into the hybridization chambers 5. The washing liquids and wash wastes leave the hybridization chambers 5 via the outlet line 13 and the already open outlet valves 14, are combined in the collection line 15 and removed through the open waste valve 17 into the waste line 16.

h) Drying the hybridized samples on the slides 27. For this purpose, only the valves 12, 14, and 17 are opened. The inert gas valve 50 is then opened and the distribution line 10, the inlet lines 11, the hybridization chambers 5, the outlet lines 13, and the collection line 15 are flushed with inert gas via the open waste valve 17 and the waste line 16 until the samples are dry.

The finished samples may then be removed.

As an alternative to the method step h) just described, the hybridized samples are dried on the slides 27 by opening only the valves 12, 14, and 21. The inert gas valve 50 is then opened and the distribution line 10, the inlet lines 11, the hybridization chambers 5, the outlet lines 13, and the collection line 15 are flushed with inert gas via the open relief valve 21, the relief line 20, the collection container 22, and the ventilation opening 23 until the samples are dry.

An alternative embodiment of the method according to the present invention, in which the second membrane 33' of the agitation device 32 may be dispensed with, is also preferred. For this purpose, another medium must assume the function of this spring element. This is achieved in that after all samples and media taking part in the hybridization are poured into the hybridization chambers 5, all valves are closed (cf. steps a-d) and the outlet valves 13 are then opened again. The volume of the collection line 15 filled with air and the directly adjoining part of the waste line 16 are thus connected to the volumes of the hybridization chambers 5 filled with liquid. The air enclosed between the closed valves 17, 19, and 21 and the specimen liquids in the hybridization chambers 5 is elastically compressible and thus forms the desired spring element.

Alternatively, the step c) may be performed using an inert gas (e.g., $N_2$): in this case, chemical interactions between the gaseous elastic element $N_2$ and the samples may be excluded.

Physical Exemplary Embodiment

In a first series of experiments, the physical foundations were investigated. For this purpose, several hundred slides were processed without samples. The O-ring seals 28, preferably made of an elastomer such as neoprene, silicone, lathed PTFE, polyethylene, or Viton, all successfully prevented liquid loss. The basic requirement is, of course, that the contact pressure on the cover 26, the O-ring 28, and the slides 27 is sufficiently large, i.e., significantly higher than the chamber pressure generated. The hybridization chambers 5 used include an area of 21×65 mm between the cover 26 and the slide 27. The chamber pressure was increased by 1 bar, i.e., by $10^5$ N/$m^2$ above the normal pressure of the surroundings. For a real effective area of 13.65 $cm^2$ or $1.365 \times 10^{-3}$ $m^2$, a force of more than 136.5 N and/or approximately 13.9 kp per hybridization chamber 5 must be applied so that they cannot open spontaneously. It is assumed that other types of seals and sealing materials will suffice and prevent a liquid leak if a closing force selected to correspond to the excess pressure in the hybridization chamber 5 is exerted on the cover 26, the seal 28, and the slide 27.

While air bubbles were regularly observed in the standard device SN22 in the course of the processing of slides having hydrophobic surfaces, no air bubbles of this type were detected in the prototypes according to the present invention.

Biological Exemplary Embodiment

Two systems were used in parallel in time and independently of one another to perform an example of a hybridization performed according to the present invention under elevated pressure. They were a standard device of the applicant (Tecan HS 400, serial number 22; called SN22 for short), which was operated at normal pressure, and a prototype according to the present invention (called PT3 for short), which was operated at a chamber pressure elevated by 0.8 to 1.0 bar. Both devices were equipped with agitation mechanisms which corresponded to one another, as was described in detail further above. This agitation device 32 in SN22 was operated using an agitation pressure of approximately 0.5 bar, and that in PT3 using approximately 1.5 bar. In both devices, the maintenance of the precise temperature was checked beforehand; they were operated using exactly identical parameters (e.g., temperatures) (except for the differences noted because of the test). This allowed direct conclusions of the causes to be made from the results achieved.

The hybridization procedure (buffer preparation, specimen injection, program definition on the hybridization systems used) was performed according to the technical instructions of Alopex (ALOPEX GmbH, Fritz-Hornschuch-Str. 9, D-95326 Kulmbach, Federal Republic of Germany). Two slides 27 were inserted into each of the hybridization systems SN22 and PT3 and processed at 43° C. or at 61° C. The results of the following process samples were discussed:

| | |
|---|---|
| 43° C. | 43° C. |
| HS 400 SN22 | HS 400 PT3 |
| Slides #29, #31 | Slides #24, #27 |
| 61° C. | 61° C. |
| HS 400 SN22 | HS 400 PT3 |
| Slides #33, #34 | Slides #35, #37 |

A test kit "HybCheck" from Alopex having the kit batch number 040524 was used. This test kit is used to check the hybridization systems and is designed so that the hybridization temperatures are predefined and the "OK" signals are only output if the temperatures provided and the relevant test parameters in regard to washing, agitation, and trying are maintained exactly. The samples immobilized on the slides 27 were oligonucleotides here, whose sensitivity to temperature differences is known.

The program executed for each sample run was, in detail, as follows:

a) Preparing the "HybCheck" washing buffers 1 and 2 according to the manufacturer instructions;
b) Dissolving lyophilized, fluorescence-marked oligonucleotides in 250 μl HybCheck buffer preheated to a hybridization temperature (43° C. or 61° C.) for the hybridization;
c) Inserting 2 slides (each having 6 sub-arrays) at positions 1 and 2 in each hybridization system, using the large hybridization chambers (63.5 mm×20 mm);
d) Closing the hybridization chambers and starting the hybridization program;
e) Hybridization program:
   1. First washing at 43° C. or 61° C., duration 30 seconds;
   2. Injection of 105 μl of the oligonucleotide solution into each chamber at 43° C. or 61° C.;
   3. Hybridization at 43° C. or 61° C.; with strong agitation and for 60 minutes;
   4. Washing step 1 at 23° C. (channel 1) for 30 seconds; suctioning for 30 seconds; 2 repetitions;
   5. Washing step 2 at 23° C. (channel 2) for 30 seconds; suctioning for 30 seconds; 2 repetitions;
   6. Drying the slides for 3 minutes at 23° C.;
f) After ending the hybridization, both slides were removed and inserted into a laser scanner (Tecan LS400);
g) Measurement settings of the laser scanner:

| | | |
|---|---|---|
| 1. | Scan mode: | single wavelength |
| 2. | Laser wavelength: | 543 nm (green) |
| 3. | Filter wavelength: | 590 nm |
| 4. | Gain: | 165 |
| 5. | Autofocus mode: | HS autofocus, level 1 |
| 6. | Scan resolution: | 10 μm |
| 7. | Pinhole: | Small |
| 8. | Oversampling factor: | 1 |

h) After measurement in the laser scanner, the raw data obtained was analyzed as follows:

Hybridization at 43° C.:

1. 6 sub-arrays (6×9 spots) on a slide (microslide)
2. Perfect match (PM) at 43° C.: 24 spots per slide (4 per sub-array)
3. Mismatch 1 (MM1) at 43° C.: 24 spots per slide (4 per sub-array)
4. Mismatch 2 (MM2) at 43° C.: 24 spots per slide (4 per sub-array)

5. Negative controls: 36 spots per slide (6 per sub-array)
6. The arithmetic mean, the standard deviation, and the CV were calculated for all PMs and MM1s per microslide (24 individual values).

In this case: CV=(standard deviation/arithmetic mean)×100

7. Discrimination PM:MM1 (1:5) and discrimination PM:MM2 (1:20) calculated
8. The CV value and the discrimination values specified as "OK" (if CV over an entire slide<18%) or "failed".

Hybridization at 61° C.:

1. 6 sub-arrays (6×9 spots) on a slide (microslide)
2. Perfect match (PM) at 61° C.: 24 spots per slide (4 per sub-array)
3. Mismatch 1 (MM1) at 61° C.: 24 spots per slide (4 per sub-array)
4. Mismatch 2 (MM2) at 61° C.: 24 spots per slide (4 per sub-array)
5. Negative controls: 36 spots per slide (6 per sub-array)
6. The arithmetic mean, the standard deviation, and the CV were calculated for all PMs and MM1s per microslide (24 individual values).

In this case: CV=(standard deviation/arithmetic mean)×100

7. Discrimination PM:MM1 (1:5) and discrimination PM:MM2 (1:20) calculated
8. The CV value and the discrimination values specified as "OK" (if CV over an entire slide<18%) or "failed".

The following results were achieved:

43° C./HS 400 SN22

| | |
|---|---|
| CV perfect match | OK |
| CV mismatch 1 | OK |
| Discrimination perfect match and mismatch 1 | OK |
| Discrimination perfect match and mismatch 2 | OK |
| Spot quality | OK |
| Negative controls | OK |

No gradient was observed.

43° C./HS 400 PT3

| | |
|---|---|
| CV perfect match | OK |
| CV mismatch 1 | OK |
| Discrimination perfect match and mismatch 1 | OK |
| Discrimination perfect match and mismatch 2 | OK |
| Spot quality | OK |
| Negative controls | OK |

No gradient was observed.

61° C./HS 400 SN22

| | |
|---|---|
| CV perfect match | OK |
| CV mismatch 1 | OK |
| Discrimination perfect match and mismatch 1 | OK |
| Discrimination perfect match and mismatch 2 | OK |
| Spot quality | #33 FAILED, #34 OK |
| Negative controls | OK |

No gradient was observed.

61° C./HS 400 PT3

| | |
|---|---|
| CV perfect match | OK |
| CV mismatch 1 | OK |
| Discrimination perfect match and mismatch 1 | OK |
| Discrimination perfect match and mismatch 2 | OK |
| Spot quality | FAILED |
| Negative controls | OK |

No gradient was observed.

The results shown do not only confirm that the two devices used provide very usable results. Rather, the results achieved in the two devices SN22 and PT3 (ordered according to temperature) are so similar to that an influence of the elevated pressure on the hybridization may be excluded.

The method according to the present invention is not restricted to use in hybridization chambers. It may also be applied and/or used in other devices to prevent the occurrence of undesired air bubbles there. Such devices or instruments may originate from the field of microfluidic technology, for example, such as "lab on a chip" systems.

What is claimed is:

1. A method for preventing air bubbles in an essentially gap-shaped hybridization chamber of a system for hybridizing nucleic acid samples, proteins, or tissue sections that are immobilized on slides, the method comprising the steps of:

(a) providing an essentially gap-shaped hybridization chamber between a slide and a cover, the cover being positioned in relation to the slide in such a way that the hybridization chamber is sealed to surrounding air;

(b) essentially filling the hybridization chamber as provided in step (a) with a liquid;

(c) building-up a chamber pressure in the hybridization chamber with a pressure device of said system; and (d) keeping the chamber pressure at a pressure of at least 100 mbar above the normal atmospheric pressure existing in the surrounding air during a hybridization procedure.

2. The method according to claim 1, wherein the chamber pressure is kept at between 100 mbar and 1.4 bar above the surrounding air pressure.

3. The method according to claim 1, wherein the chamber pressure is generated using a liquid or using a gas.

4. The method according to claim 3, wherein the liquid for generating the chamber pressure is a hybridization medium, which is pressed by a feed pump into a distribution line and via inlet valves against the liquid in the hybridization chamber.

5. The method according to claim 3, wherein the gas for generating the chamber pressure is air suctioned in by a feed pump via an aeration valve or an inert gas stored in a container, this gas being pressed against the liquid in the hybridization chamber via a distribution line and via inlet valves.

6. The method according to claim 2, which further comprises the step of:

(e) intermittently building-up an agitation pressure in a pressure chamber, wherein the agitation pressure is 0.5 bar to 1 bar higher than the chamber pressure, wherein said pressure chamber is positioned in the cover and separated from an agitation chamber by a membrane, and wherein the agitation chamber is connected to the hybridization chamber via an agitation line.

7. The method according to claim 6, which further comprises the step of:

(f) counteracting this agitation pressure with a spring element that is provided as a second membrane positioned in the cover or as a volume filled with a gas.

* * * * *